(12) United States Patent
Sartor et al.

(10) Patent No.: US 10,639,400 B2
(45) Date of Patent: *May 5, 2020

(54) COUPLING A BODY CONDUIT TO TISSUE

(71) Applicant: COVIDIEN LP, Mansfield, MA (US)

(72) Inventors: Joe D. Sartor, Longmont, CO (US);
Anthony B. Ross, Boulder, CO (US);
Stephen Wohlert, Branford, CT (US)

(73) Assignee: COVIDIEN LP, Mansfield, MA (US)

( * ) Notice: Subject to any disclaimer, the term of this patent is extended or adjusted under 35 U.S.C. 154(b) by 134 days.

This patent is subject to a terminal disclaimer.

(21) Appl. No.: 15/840,218

(22) Filed: Dec. 13, 2017

(65) Prior Publication Data

US 2018/0110902 A1 Apr. 26, 2018

Related U.S. Application Data

(62) Division of application No. 14/853,652, filed on Sep. 14, 2015, now Pat. No. 9,861,726.

(Continued)

(51) Int. Cl.

| | |
|---|---|
| *A61L 27/24* | (2006.01) |
| *A61F 2/04* | (2013.01) |
| *A61L 27/54* | (2006.01) |
| *A61B 17/11* | (2006.01) |
| *A61M 25/00* | (2006.01) |

(Continued)

(52) U.S. Cl.
CPC ............. *A61L 27/54* (2013.01); *A61B 17/11* (2013.01); *A61L 27/24* (2013.01); *A61L 27/56* (2013.01); *A61M 25/0017* (2013.01); *A61B 2017/00274* (2013.01); *A61B 2017/00292* (2013.01); *A61B 2017/00884* (2013.01); *A61B 2017/1135* (2013.01); *A61F 2/04* (2013.01); *A61F 2/958* (2013.01); *A61F 2002/047* (2013.01); *A61F 2002/9583* (2013.01); *A61L 27/3683* (2013.01);

(Continued)

(58) Field of Classification Search
CPC .................................................. A61F 2002/047
See application file for complete search history.

(56) References Cited

U.S. PATENT DOCUMENTS

| | | | |
|---|---|---|---|
| 5,762,966 A | 6/1998 | Knapp, Jr. et al. | |
| 6,477,426 B1 | 11/2002 | Fenn et al. | |

(Continued)

FOREIGN PATENT DOCUMENTS

| | | | |
|---|---|---|---|
| EP | 2258445 A1 | 12/2010 | |
| WO | 9205697 A1 | 4/1992 | |

(Continued)

*Primary Examiner* — Megan Y Wolf
(74) *Attorney, Agent, or Firm* — Carter, DeLuca & Farrell LLP

(57) ABSTRACT

A method for coupling a body conduit to tissue includes engaging an implant about an outer surface of a catheter. The implant receives a bioactive agent having tissue growth properties. The method involves inserting the catheter through the body conduit and into a tissue opening across a resected area, positioning the implant in the resected area, inflating a balloon to anchor the catheter within the tissue opening such that the implant bridges the body conduit and the tissue opening across the resected area, and maintaining the catheter and the implant in vivo to enable the bioactive agent to secure the implant in the resected area to permanently bridge the body conduit and the tissue opening.

17 Claims, 6 Drawing Sheets

Related U.S. Application Data

(60) Provisional application No. 62/050,509, filed on Sep. 15, 2014.

(51) Int. Cl.
*A61L 27/56* (2006.01)
*A61F 2/958* (2013.01)
*A61L 27/36* (2006.01)
*A61L 27/38* (2006.01)
*A61B 17/00* (2006.01)

(52) U.S. Cl.
CPC ..... *A61L 27/3834* (2013.01); *A61L 2300/414* (2013.01); *A61L 2430/22* (2013.01)

(56) References Cited

U.S. PATENT DOCUMENTS

| | | |
|---|---|---|
| 7,862,552 B2 | 1/2011 | McIntyre et al. |
| 8,206,280 B2 | 6/2012 | Evans et al. |
| 8,337,485 B2 | 12/2012 | Ludlow et al. |
| 8,491,526 B2 | 7/2013 | Cronin et al. |
| 9,861,726 B2 | 1/2018 | Sartor et al. |
| 2002/0077594 A1 | 6/2002 | Chien et al. |
| 2004/0091461 A1* | 5/2004 | Kropp .............. A61F 2/02 424/93.7 |
| 2005/0165378 A1 | 7/2005 | Heinrich et al. |
| 2006/0264912 A1 | 11/2006 | McIntyre et al. |
| 2008/0269547 A1 | 10/2008 | Hortenstine |
| 2009/0137862 A1 | 5/2009 | Evans et al. |
| 2010/0034867 A1 | 2/2010 | Herweck et al. |
| 2010/0131075 A1 | 5/2010 | Ludlow et al. |
| 2010/0168621 A1 | 7/2010 | Neville |
| 2010/0184220 A1* | 7/2010 | Ram-Liebig ........ A61L 27/3808 435/395 |
| 2010/0222802 A1 | 9/2010 | Gillespie, Jr. et al. |
| 2011/0190679 A1 | 8/2011 | Humes et al. |
| 2011/0212090 A1 | 9/2011 | Pedersen et al. |
| 2011/0282324 A1 | 11/2011 | Kurokawa et al. |
| 2011/0282381 A1 | 11/2011 | Cronin et al. |
| 2012/0027727 A1 | 2/2012 | Hall et al. |
| 2012/0150179 A1 | 6/2012 | Feinberg et al. |
| 2013/0071445 A1 | 3/2013 | Zupkas et al. |
| 2015/0359537 A1 | 12/2015 | Huang et al. |

FOREIGN PATENT DOCUMENTS

| | | |
|---|---|---|
| WO | 2011140137 A2 | 11/2011 |
| WO | 201209703 A2 | 1/2012 |

* cited by examiner

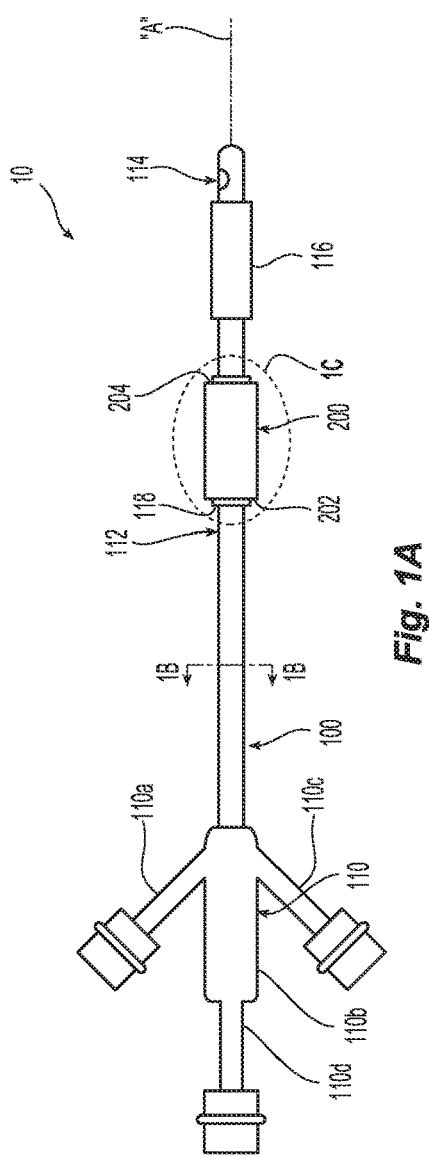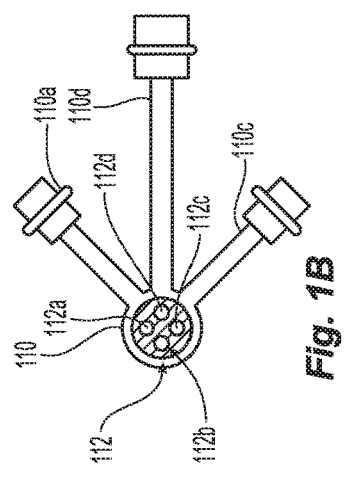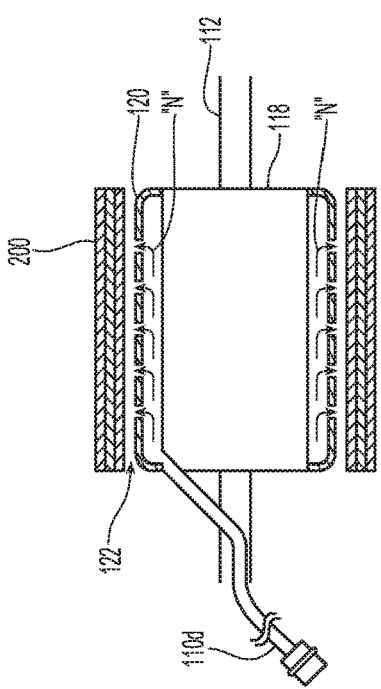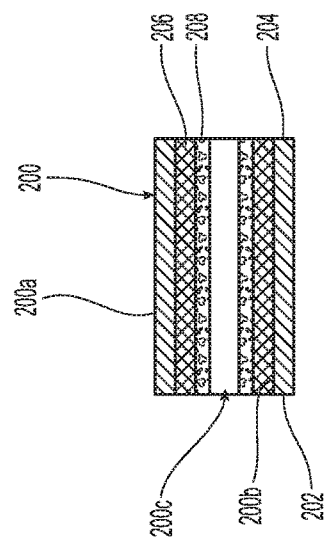

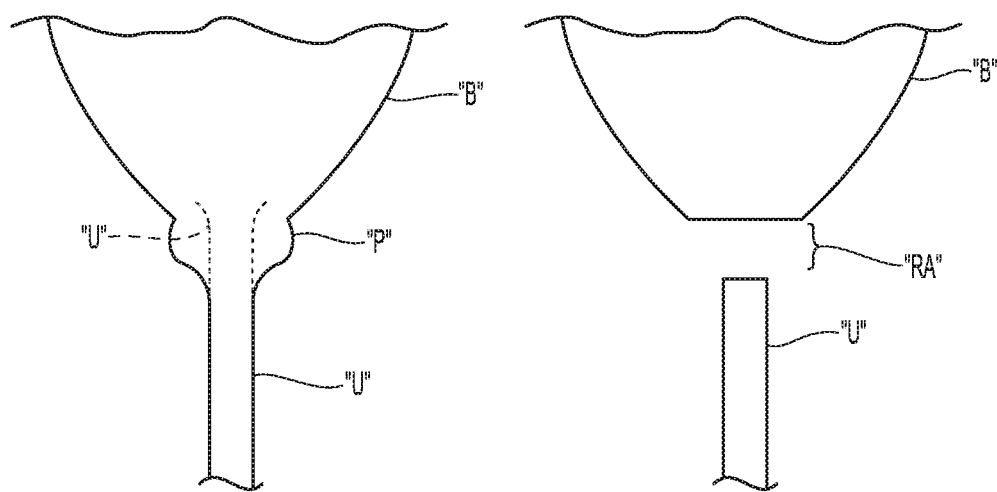
*Fig. 3A*  *Fig. 3B*
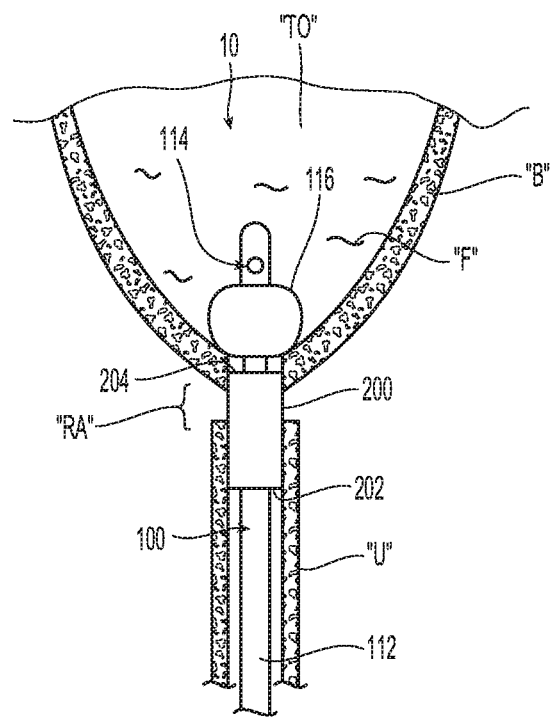
*Fig. 3C*

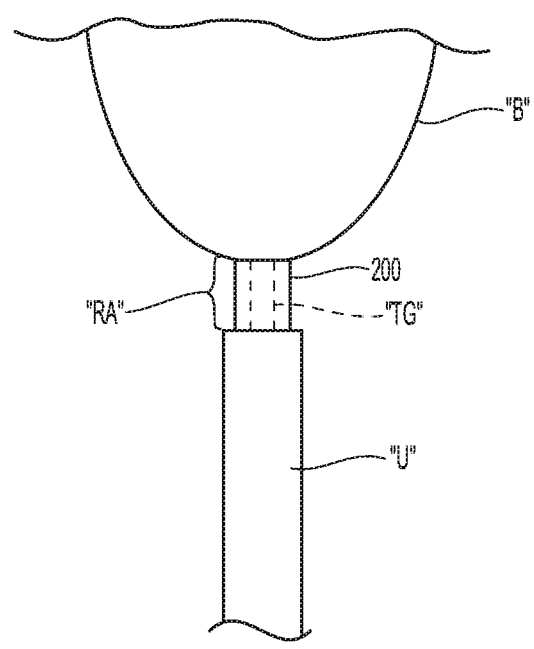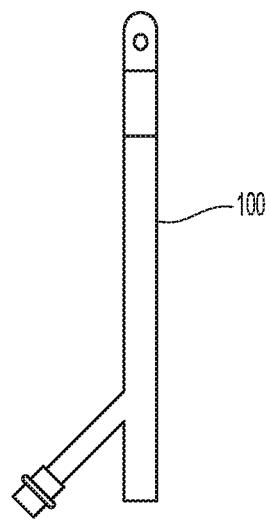
Fig. 3D

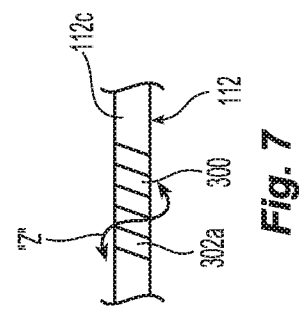
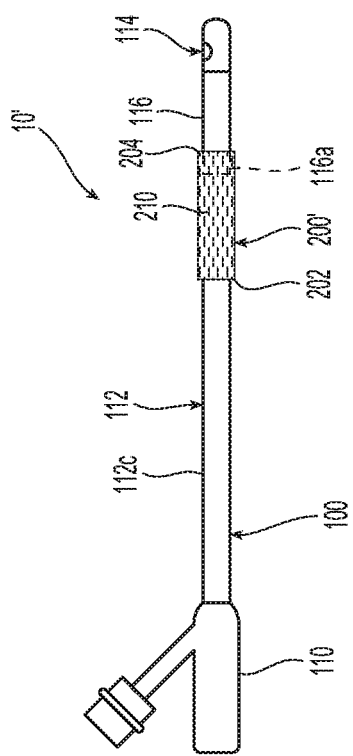
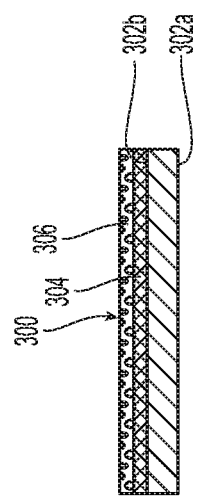
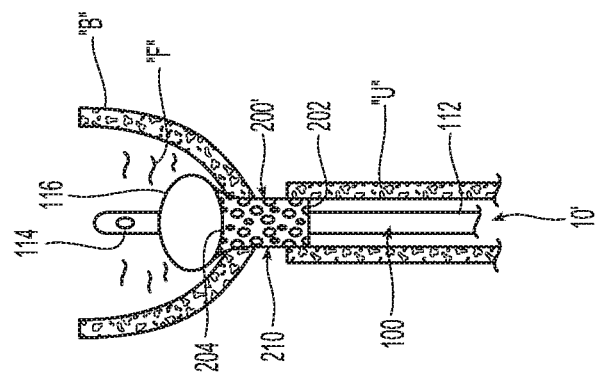

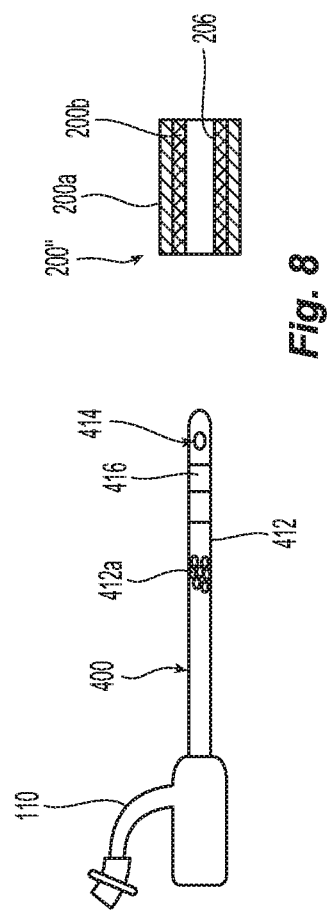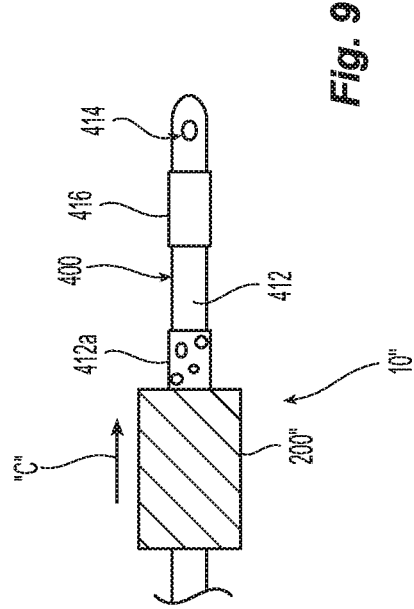
Fig. 8
Fig. 9

COUPLING A BODY CONDUIT TO TISSUE

CROSS REFERENCE TO RELATED APPLICATIONS

This application is a divisional application of U.S. patent application Ser. No. 14/853,652, filed on Sep. 14, 2015, now U.S. Pat. No. 9,861,726, which claims the benefit of U.S. Provisional Application Ser. No. 62/050,509, filed Sep. 15, 2014, the entire contents of each of which are incorporated by reference herein.

This application is related to U.S. patent application Ser. No. 14/853,597, filed on Sep. 14, 2015, the entire contents of which are incorporated by reference herein.

TECHNICAL FIELD

The present disclosure relates to surgical devices, systems, and methods for performing prostatectomies, and, more particularly, to surgical devices, systems, and methods for coupling a urethra to a bladder after resecting a prostate.

BACKGROUND

Prostatectomy is the surgical removal of all or part of the prostate for men with early-stage disease or cancer that is confined to the prostate. In removing the prostate, the portion of the urethra that extends through the prostate becomes resected so that an anastomosis (e.g., stitching, stapling, etc.) is required to reconnect the urethra to the bladder. To effectuate a reliable anastomosis, the bladder neck is often pulled down into the pelvic cavity resulting in distortion of the bladder. Distortion of the bladder anatomy can lead to reduced bladder functionality or even incontinence. In cases of extensive prostate resection, the bladder neck may need to be removed entirely, making anastomosis to the bladder impossible.

After surgery, a catheter such as a Foley catheter is inserted through the urethra and anchored in the bladder by a balloon to maintain urine flow through the catheter while the surgical site of the anastomosis heals. Even if the anastomosis procedure is successful, post-operative complications such as anastomotic failure and/or infections can occur at the anastomotic site, necessitating further procedures or prolonged catheterization. When an anastomosis fails or otherwise cannot be performed, the patient may be subject to permanent catheterization.

SUMMARY

Accordingly, new devices, systems, and methods that improve prostatectomy procedures would be desirable. For instance, eliminating the anastomosis step in a prostatectomy would reduce operative time, post-operative complications, and infections. As a result, patient recovery time is shortened and patient comfort is maximized.

In one aspect, the present disclosure relates to a catheter assembly for coupling a body conduit to tissue. For example, in a prostatectomy procedure, a catheter and an implant of the catheter assembly are positionable in vivo to enable the implant to permanently act as a bridge between a patient's urethra and bladder after a resection of the patient's prostate.

The catheter assembly may include an elongated member such as a catheter, a balloon, first and second ports, and an implant. In some embodiments, the catheter assembly may include first and second balloons. The elongated member has an outer surface and an inner surface. The outer surface defines a distal opening. The balloon is supported on the outer surface of the elongated member adjacent to the distal opening. The first port is defined in a proximal end of the elongated member and is in fluid communication with the distal opening. The second port is defined in the proximal end of the elongated member and is in fluid communication with the balloon.

The implant is selectively positionable about the outer surface of the elongated member and is configured to receive a bioactive agent having tissue growth properties. The implant is configured to act as a bridge between the body conduit and the tissue and is separable from the catheter assembly. The implant may be at least partially formed from a collagen or a collagen copolymer. In certain embodiments, the implant may include a biologic derived from a decellularized tissue source. In some embodiments, the implant may have a tubular or planar configuration that engages the outer surface of the elongated member. In certain embodiments, the bioactive agent has bacteriostatic properties. In some embodiments, the implant may be at least partially formed from a decellularized biologic material. It is also recognized that the catheter may be useful for urethral reconstruction often associated strictures occurring from any number of causes but usually reconstructed with buccal mucosa where supporting an autologous graph and maintaining strain to the diameter of the urethra is important.

The bioactive agent may include one or more of epithelial cells, stem cells, epidermal growth factors, and fibroblast growth factors. In certain embodiments, the bioactive agent is impregnated within the implant.

The outer surface of the elongated member may be configured to receive the bioactive agent and the implant may be positionable over the outer surface of the elongated member so that at least a portion of an inner surface of the implant engages the bioactive agent.

In some embodiments, a distal portion of the implant is positioned over a proximal portion of the balloon and a proximal portion of the implant is positioned over the outer surface of the elongated member. The balloon may be configured to expand the implant in response to inflation of the balloon to anchor the distal portion of the implant against tissue. The implant may define a plurality of slits configured to facilitate expansion of the implant. It is appreciated that positioning the implant in close proximity to surrounding vascularized tissue is essential to growth of the implant and prevention of necrosis of the implant.

In certain embodiments, the implant is seeded with extracted cells from a patient prior to implantation. The seeded implant may be incubated prior to implantation.

According to one aspect, the present disclosure relates to a method for coupling a body conduit to tissue. The method includes engaging an implant about an outer surface of a catheter, the implant configured to receive a bioactive agent having tissue growth properties; inserting the catheter through the body conduit and into a tissue opening across a resected area; positioning the implant in the resected area; inflating a balloon to anchor the catheter within the tissue opening such that the implant bridges the body conduit and the tissue opening across the resected area; and maintaining the catheter and the implant in vivo to enable the bioactive agent to secure the implant in the resected area and to permanently bridge the body conduit and the tissue opening.

The method may involve deflating the balloon to remove the catheter after the implant is permanently secured in vivo. The method may include sliding the implant over the outer surface of the catheter to position the implant on the outer surface of the catheter, temporarily fixing it to the catheter such as with an un-knotted stay suture, wherein the catheter includes a Foley catheter. The method may involve impregnating the outer surface of the catheter with the bioactive agent and positioning the implant over an impregnated portion of the outer surface of the catheter. Inserting the catheter may include advancing the catheter through an unresected portion of a resected urethra and into a bladder such that the implant bridges a resected area defined between the unresected portion of the resected urethra and the bladder.

The method may involve inflating a second balloon to engage the implant with surrounding tissue. The method may include inflating a second balloon in a pulsatile manner. The method may include exchanging fluid through a conduit in communication with the implant.

In another aspect, the present disclosure relates to a method for implanting a xenograft in a human body. The method includes decellularizing a xenograft to form a collagen-based scaffold, seeding the collagen-based scaffold with human stem cells, changing a morphology of the human stem cells to render the collagen-based scaffold suitable for implantation within the human body, mounting the collagen-based scaffold on a catheter, and implanting the collagen-based scaffold within the human body to provide a bridge between tissues of the human body.

The method may involve harvesting the xenograft from porcine tissue. The porcine tissue may be a porcine urethra. In some embodiments, changing a morphology of the human stem cells includes differentiating of the human stem cells. Morphology changes can be effectuated via the use of pulsatile stress, growth factors, and/or signaling proteins. Scaffold structure and/or material elasticity may also effect morphology changes. Differentiating of the human stem cells may be conducted ex vivo.

In yet another aspect of the present disclosure, a catheter system includes a catheter, a biologic implant supported on the catheter, and a fluid conduit defined in the catheter and configured to exchange fluid between the catheter and the biologic implant. In some embodiments, the catheter supports an inflatable balloon having a porous membrane mounted thereon. The porous membrane may be in fluid communication with the fluid conduit.

According to still another aspect of the present disclosure, a catheter includes a body member having an inner surface and an outer surface, a first port defined in the body member, a balloon disposed about the outer surface of the body member, and a porous membrane supported on the balloon. The balloon may be configured to position an implant in close proximity to surrounding tissue. The porous membrane may be in communication with the first port to transport fluids and bioactive agents from the first port through the porous membrane.

In aspects, the catheter may further include a second port defined in the catheter and in communication with the balloon to communicate inflation fluid between the second port and the balloon.

In aspects, the balloon is configured to be inflated in a pulsatile manner.

In aspects, the catheter may further include a second balloon supported on the body member and configured to anchor a distal end of the body member within a conduit or an organ.

The body member may include a proximal end and a distal end. The distal end of the body member may define a distal opening in communication with the proximal end of the body member to enable transportation of fluids through the distal opening.

An implant may be supported on the balloon. The implant may be configured to act as a tissue scaffold in a repair or replacement of a natural anatomical conduit.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 1A is a perspective view of one embodiment of a catheter assembly in accordance with the principles of the present disclosure;

FIG. 1B is a cross-sectional view of the catheter assembly of FIG. 1A as taken along line segment 1B-1B;

FIG. 1C is an enlarged view, in partial cross-section, of the indicated area of detail shown in FIG. 1A;

FIG. 2 is a cross-sectional view of an implant of the catheter assembly of FIG. 1A;

FIGS. 3A-3D are progressive views of a prostatectomy procedure in accordance with the principles of the present disclosure;

FIG. 4 is a perspective view of another embodiment of a catheter assembly in accordance with the principles of the present disclosure;

FIG. 5 is a partial, cross-sectional view showing the catheter assembly of FIG. 4 positioned in vivo;

FIG. 6 is a side view of another embodiment of an implant;

FIG. 7 is a side view illustrating the implant of FIG. 6 as positioned on a catheter of the catheter assembly of FIG. 1A;

FIG. 8 is a perspective view, with parts separated, of another embodiment of a catheter assembly with an implant thereof shown in cross-section;

FIG. 9 is an enlarged perspective view of a distal portion of the catheter assembly of FIG. 8.

DETAILED DESCRIPTION

Figure 10:
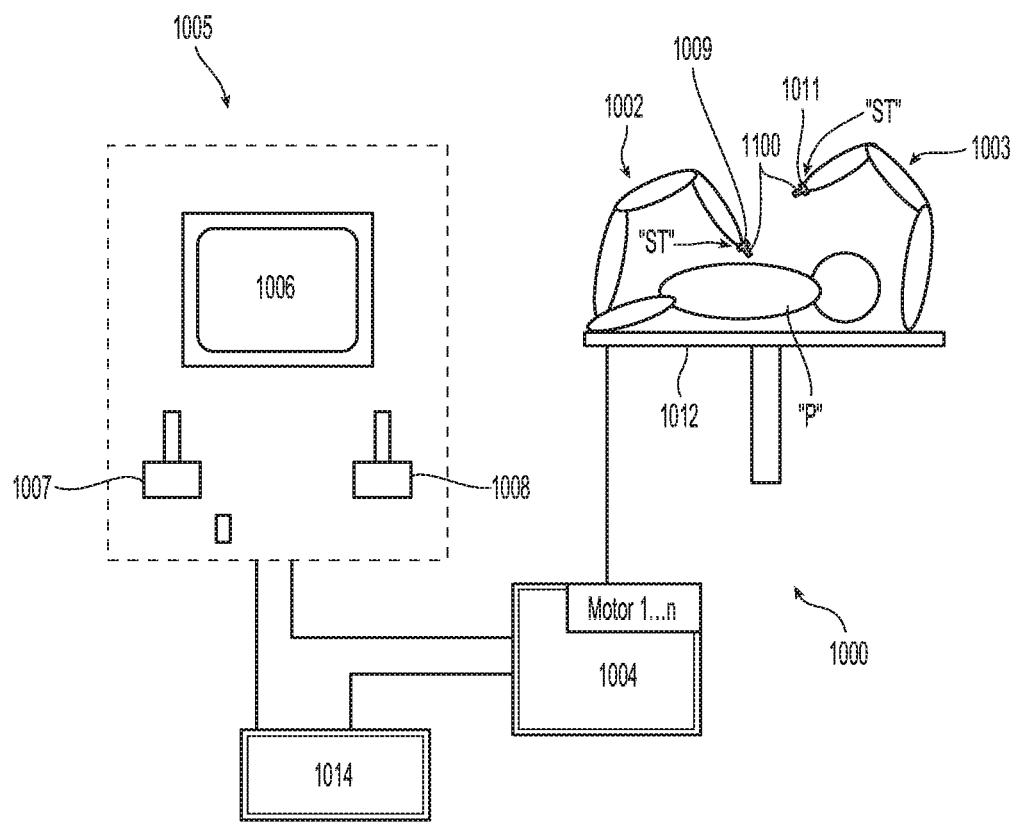
FIG. 10 is a schematic illustration of a medical work station and operating console in accordance with the present disclosure.

Particular embodiments of the present disclosure are described hereinbelow with reference to the accompanying drawings in which like reference numerals designate identical or corresponding elements in each of the several views. As used herein the term "distal" refers to that portion of the system, apparatus and/or device, or component thereof, that are farther from the user, while the term "proximal" refers to that portion of the system, apparatus and/or device, or component thereof, that are closer to the user. In the following description, well-known functions or constructions are not described in detail to avoid obscuring the present disclosure in unnecessary detail.

Turning now to FIGS. 1A-1C, one embodiment of a catheter assembly 10 includes a catheter 100 (e.g., a Foley catheter) and an implant 200 supported thereon. Catheter 100 defines a longitudinal axis "A" and includes a manifold 110 and an elongated member 112 that extends distally from manifold 110. Manifold 110 includes a first port 110a and a second port 110b that extend proximally therefrom. Elongated member 112 defines a first lumen 112a having a proximal end in fluid communication with first port 110a of manifold 110 and a distal end in communication with a distal opening 114 defined by elongated member 112. Elongated member 112 defines a second lumen 112b having a proximal end in fluid communication with second port 110b of manifold 110 and a distal end in fluid communication with a distal balloon 116 supported on an outer surface of elongated member 112. Elongated member 112 further defines a third lumen 112c having a proximal end in communication with a third port 110c and a distal end in fluid communication with a proximal balloon 118 supported on an outer surface of elongated member 112 at a location proximal to distal balloon 116. Proximal balloon 118 is configured to at least partially overlap a gap in urethra length (e.g., resected area "RA" shown in FIG. 3B), which may be surgically or otherwise created. Proximal balloon 118 and distal balloon 116 may be adjacent or at any space needed to achieve the urethral repair specific to the patient's anatomy. A porous membrane 120 is supported on proximal balloon 118 between an outer surface of the proximal balloon 118 and an inner surface of the implant 200.

Elongated member 112 also defines a fourth lumen 112d in communication with a port 110d at a proximal end thereof and a fluid passage 122 at a distal end thereof. Fluid passage 122 is defined between the outer surface of proximal balloon 118 and the inner surface of implant 200. The fluid passage 122 is arranged to facilitate drainage of fluids from, and/or transfer of fluids and/or nutrients "N" to, implant 200. The porous membrane 120 is configured to enable these fluids and/or nutrients "N" therethrough.

As seen in FIG. 2, implant 200 has a tubular configuration and may be at least partially formed of a fiber of collagen, a collagen copolymer, chitosan, polyvinyl alcohol (PVA), poly(acrylic acid) (PAA) and β-glycerol phosphate, poly(L-lactic acid) (PLLA), polycaprolactone (PCL), poly (d, 1-lactide-co-glycolide) (PLGA) and/or the like material. Implant 200 may be a tubular biomaterial or tube rolled from a biomaterial derived from porcine (e.g., urethra, skin, bowel, pericardium, etc.) and/or may be related to previous art known in commercial Medtronic Permacol products. Permacol derived materials have the advantage of being decellularized, but retain extracellular matrix and important growth factors. Durability of the Permacol processed material may enable crosslinking of tissue matrix to provide durability if ingrowth is delayed by insufficient blood supply.

Implant 200 extends between proximal and distal ends 202, 204 and includes an outer surface 200a and an inner surface 200b that defines a lumen 200c. Inner surface 200b supports one or more bioactive agents 206 having tissue growth properties such as, for example: epithelial cells, stem cells, epidermal growth factors, and/or fibroblast growth factors. Inner surface 200b may also support one or more bioactive agents 208 having bacteriostatic properties, (e.g., chitosan) to prevent infection (e.g., urinary tract infection). As can be appreciated, one or more of these bioactive agents 206, 208 may have both tissue growth and bacteriostatic properties. In some embodiments, one or more of these bioactive agents are layered on inner surface 200b. In certain embodiments, one or more of these bioactive agents are impregnated within implant 200. The bioactive agents of any of the presently described catheter assemblies may be any substance or mixture of substances that have clinical use. The bioactive agents may invoke a biological action, exert a biological effect, or play a role in one or more biological processes. The type and amount of bioactive agent(s) used will depend, among other factors, on the particular site and condition to be treated.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors, and enzymes.

In some embodiments, the bioactive agent may be a growth factor, such as transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors. In some embodiments, members of the transforming growth factor (TGF) supergene family, which are multifunctional regulatory proteins, are utilized. Members of the TGF supergene family include the beta transforming growth factors (for example, TGF-β1, TGF-β2, TGF-β3); bone morphogenetic proteins (for example, BMP-1, BMP-2, BMP-3MP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)); Inhibins (for example, Inhibin A, Inhibin B); growth differentiating factors (for example, GDF-1); and Activins (for example, Activin A, Activin B, Activin AB). Vascular growth factor (VGF) can be important to reestablishing blood supply to a graft and/or surrounding tissue, the absence of which is a leading cause of biological graft failure.

In some embodiments, the bioactive agent is a biologic or cell specific ligand capable of attracting or recruiting specific cell types, such as smooth muscle cells, stem cells, immune cells, and the like.

Suitable antimicrobial agents which may be included as a bioactive agent include triclosan, also known as 2,4,4'-trichloro-2'-hydroxydiphenyl ether; chlorhexidine and its salts, including chlorhexidine acetate, chlorhexidine gluconate, chlorhexidine hydrochloride, and chlorhexidine sulfate; silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine; polymyxin; tetracycline; aminoglycosides such as tobramycin and gentamicin; rifampicin; bacitracin; neomycin; chloramphenicol; miconazole; quinolones such as oxolinic acid, norfloxacin, nalidixic acid, pefloxacin, enoxacin and ciprofloxacin; penicillins such as oxacillin and pipracil; nonoxynol 9; fusidic acid; cephalosporins; and combinations thereof. In addition, antimicrobial proteins and peptides such as bovine lactoferrin and lactoferricin B may be included as a bioactive agent in the present disclosure.

Other bioactive agents include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; antispasmodics; anticholinergic agents (e.g., oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists such as naltrexone and naloxone; anti-cancer agents (i.e., to limit uncontrolled growth); anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; chemotherapeutics (i.e., to limit uncontrolled growth); estrogens; antibacterials; antibiotics; antifungals; anti-virals; anticoagulants; anticonvulsants; antidepressants; antihistamines; and immunological agents.

Other examples of suitable bioactive agents include viruses and cells; peptides; polypeptides and proteins, as well as analogs, muteins, and active fragments thereof; immunoglobulins; antibodies; cytokines (e.g., lymphokines, monokines, chemokines); blood clotting factors; hemopoietic factors; interleukins (IL-2, IL-3, IL-4, IL-6); interferons (β-IFN, α-IFN and γ-IFN); erythropoietin; nucleases; tumor necrosis factor; colony stimulating factors (e.g., GCSF, GM-CSF, MCSF); insulin; anti-tumor agents and tumor suppressors; blood proteins such as fibrin, thrombin, fibrinogen, synthetic thrombin, synthetic fibrin, synthetic fibrinogen; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); protein inhibitors; protein antagonists; protein agonists; nucleic acids such as antisense molecules, DNA, and RNA; oligonucleotides; polynucleotides; ribozymes; naturally occurring polymers including proteins such as collagen and derivatives of various naturally occurring polysaccharides such as glycosaminoglycans; peptide hydrolases such as elastase, cathepsin G, cathepsin E, cathepsin B, cathepsin H, cathepsin L, trypsin, pepsin, chymotrypsin, γ-glutamyltransferase (γ-GTP) and the like; sugar chain hydrolases such as phosphorylase, neuraminidase, dextranase, amylase, lysozyme, oligosaccharase and the like; oligonucleotide hydrolases such as alkaline phosphatase, endoribonuclease, endodeoxyribonuclease and the like.

In some embodiments, the bioactive agent may include an imaging agent such as iodine or barium sulfate, or fluorine, to allow visualization of the fluid at the time of application or thereafter through the use of imaging equipment, including X-ray, MRI, and CAT scan equipment. Other imaging agents which may be included are within the purview of those skilled in the art and include, but are not limited to, substances suitable for use in medical implantable medical devices, such as FD&C dyes 3 and 6, eosin, methylene blue, indocyanine green, or colored dyes normally found in synthetic surgical sutures. Suitable colors include green and/or blue because such colors may have better visibility in the presence of blood or on a pink or white tissue background.

In use such as in a prostatectomy procedure, as illustrated in FIGS. 3A-3C, tissue such as a prostate "P" or portions thereof, and portions of a body conduit such as a urethra "U," are surgically removed from a resected area "RA." Prior to insertion in urethra "U," one or more bioactive agents 208 (e.g., epithelial cells obtained from the patient's body) may be placed on one or more surfaces of implant 200 such as inner surface 200b. For example, a cytology brush or the like may be used to scrap the patient's body for removing epithelial cells from urethra "U" and for depositing the removed epithelial cells onto at least portions of implant 200. The epithelial cells (or any other suitable bioactive agent) may be arranged on implant 200 so as to limit undesirable tissue adhesion. Implant 200 may then be slid over catheter 100 for insertion within urethra "U." With implant 200 positioned on catheter 100, catheter assembly 10 is advanced through urethra "U," across resected area "RA," and into a tissue opening "TO" of bladder "B." Once in vivo, catheter 100 and implant 200 are positioned so that implant 200 acts as a bridge between urethra "U" and bladder "B." Once catheter assembly 10 is disposed in the desired position, inflation fluid (not shown) can be delivered through catheter 100 via second port 110b and second lumen 112b (see FIGS. 1A and 1B) to balloon 116 for inflation thereof. Inflation of balloon 116 within bladder "B" anchors catheter 100 so that implant 200 remains fixed in resected area "RA."

Proximal balloon 118 is then inflated to engage implant 200 with the abdominal tissue surrounding the target anastomosis or graph location. Inflation may be pulsed to facilitate the conditioning of cells implanted and/or entering the implant 200 in vivo. Fluid accumulation surrounding implant 200 may be selectively drained through implant 200 via the fluid passage 122 between the proximal balloon 118 and the implant 200. Alternately, the fluid passage 122 may pass nutrients or biologic agents "N" by injection through fluid passage 122. By virtue of pulsation of proximal balloon 118 and control of fluids through fluid passage 122, the catheter system is configured to form an in vivo bio reactor typical of industry applications.

Fluid "F," such as urine (or blood) that pools within bladder "B," can be drained from bladder "B" through distal opening 114 of catheter 100 and discharged through first port 110a via first lumen 112a (see FIGS. 1A and 1B). Some fluid "F" collected within the bladder "B" may seep around catheter 100 and gather in resected area "RA" between implant 200 and catheter 100. Suitable bioactive agents 206 positioned on implant 200 that have bacteriostatic properties protect against infection that could form in resected area "RA" as a result of the gathered fluid "F."

While catheter assembly 10 is fixed in vivo, and with the properties of the one or more bioactive agents 206, 208, tissue growth "TG" is formed on and/or around at least portions of implant 200 (e.g., inner surface 200b, distal and/or proximal portions of outer surface 220a, etc.) to reconnect urethra "U" to bladder "B." Tissue growth "TG" helps reform epithelial mucosal surfaces on inner surface 200b of implant 200, for example.

Tissue growth "TG" can occur along inner and/or outer surfaces 200a, 200b of implant 200 so that a proximal portion of implant 200 becomes fixed to the urethra "U" and a distal portion of implant 200 becomes fixed to the bladder "B." As can be appreciated, distal and/or proximal ends 202, 204 of implant 200 may be secured to urethra "U" using known fastening techniques such as stitching, stapling, and/or adhesive to facilitate securement of implant 200 thereto.

With reference to FIG. 3D, once implant 200 is fixedly secured in the patient's body across resected area "RA," balloon 116 can be deflated and catheter 100 can be separated from implant 200 for withdrawal from the patient's body. With catheter 100 withdrawn, implant 200 remains in the patient's body and acts as a permanent bridge between urethra "U" and bladder "B."

Turning now to FIG. 4, one embodiment of a catheter assembly 10' is illustrated. Catheter assembly 10' includes catheter 100 and an implant 200' supported thereon. Implant 200' defines a plurality of slits 210 that enable implant 200' to expand and facilitate tissue ingrowth. With implant 200' in a contracted condition as shown in FIG. 4, a distal portion 204 of implant 200' is positioned on a proximal portion 116a of balloon 116 of catheter 100 and a proximal portion 202 of implant 200' is positioned on outer surface 112c of catheter 100.

As seen in FIG. 5, once catheter assembly 10' is inserted into bladder "B," distal balloon 116 of catheter 100 is inflated, expanding implant 200 to contact surrounding abdominal tissue. Inflation of the distal balloon 116 and expansion of the implant 200 may be further facilitated by a plurality of slits 210 of implant 200' so that implant 200' can be positioned in an expanded condition with distal portion 204 of implant 200' anchored to bladder "B" as depicted in FIG. 5. Distal portion 204 may be flared outwardly relative to a remainder of implant 200' to facilitate anchoring to bladder "B." In particular, distal portion 204 of implant 200' is anchored between proximal portion 116a of balloon 116 and inner surfaces of bladder "B." Proximal end 202 of implant 200' can be secured to urethra "U" by appropriate application of suitable bioactive agents and/or using known fastening techniques such as stitching, stapling, adhesive, and/or the like as described herein. Notably, distal end 204 of implant 200' can also be further secured to bladder "B" by appropriate application of suitable bioactive agents and/or using known fastening techniques such as stitching, stapling, adhesive, and/or the like as described herein. Once implant 200' is fixedly secured in patient's body across resected area "RA," balloon 116 can be deflated and catheter 100 can be separated from implant 200' for withdrawal from the patient's body similar to that described above with respect to catheter assembly 10. Also similar to implant 200, implant 200' acts as a permanent bridge in the patient's body between a body conduit such as urethra "U" and tissue such as bladder "B" (see FIG. 3D).

With reference to FIG. 6, one embodiment of an implant 300 has a planar configuration and includes an outer surface 302a and an inner surface 302b. Inner surface 302b supports one or more bioactive agents 304, 306 which maybe be layered thereon. As depicted in FIG. 7, implant 300 can be wrapped around outer surface 112c of elongated member 112 of catheter 100, (e.g., in a spiral fashion as illustrated by arrow "Z"), to arrange the planar configuration of implant 300 into a tubular configuration with inner surface 302b of implant 300 engaged with outer surface 112c of catheter 100. In use, catheter 100 and implant 300 are positioned in vivo so that when catheter 100 is withdrawn from the patient's body, implant 300 remains in the patient's body and acts as a permanent bridge similar to that described above with respect to implants 200 and 200'.

Turning now to FIGS. 8 and 9, one embodiment of a catheter assembly 10" having a catheter 400 and an implant 200" is illustrated. Catheter 400 includes manifold 110 having an elongated shaft 412 extending distally therefrom. Elongated shaft 412 supports balloon 416 and defines distal opening 414. Elongated shaft 412 includes an outer surface having an impregnated portion 412a that supports one or more bioactive agents 208 as described herein. Implant 200" includes an outer surface 200a and an inner surface 200b that supports one or more bioactive agents 206. As illustrated by arrow "C," implant 200" is positionable over impregnated portion 412a of catheter 400 so that inner surface 200b and/or bioactive agent 206 of implant 200" engages and/or contacts impregnated portion 412a. In this regard, the one or more bioactive agents 208 of impregnated portion 412a can migrate/transfer to inner surface 200b of implant 200". In use, catheter 400 and implant 200" are positioned in vivo so that when catheter 400 is withdrawn from the patient's body, implant 200" remains in the patient's body and acts as a permanent bridge similar to that described above with respect to implants 200, 200', and 300.

Although described herein with regard to prostatectomies, the presently described devices, systems, and methods can be applied to any tissue and/or body conduit.

In some embodiments, any of the presently described implants can be formed ex vivo and implanted using the devices, systems, and/or methods presently described herein. In one example, body tissue can be a xenograft harvested from any suitable animal (e.g., porcine, bovine, etc.). For instance, a porcine urethra is harvested and decellularized to create a collagen-based scaffold (e.g., proteins, lipids, etc. are removed until only collagen or mostly collagen remains). The collagen-based scaffold may include elastin. The porcine urethra can be decellularized using any known physical treatments (e.g., temperature, force/pressure, and/or electrical disruption) and/or chemical treatments (e.g., acids, alkaline treatments, ionic/nonionic/zwitterionic detergents, etc). Once decellularized, the collagen-based scaffold can be seeded with human cells (e.g., stem cells), which may be stem cells. While the collagen-based scaffold is in a sterile environment (e.g., a sterile cell culture bag), a bioreactor can be coupled to the sterile environment to feed the collagen-based scaffold with an appropriate media including any required nutrients to sustain viability and/or growth. As the collagen-based scaffold becomes populated over time, the morphology of the human cells can be changed.

For example, the human cells can be proliferated and dedifferentiated as necessary to rebuild/regrow the human cells on the collagen-based scaffold into an epithelized urethra. Preferably, the tissue implant is configured to enable rapid ingress of the patients tissue (e.g., by fibroblast in the bulk and by spreading epithelial cells along the inner lumen of the implant). The ability to provide growth media through the membrane of the implant, as well as the ability to pulse the balloon of the implant will help in differentiating the cells in the implant and in accelerating the production of extracellular matrix (ECM)

In the hospital, cells may be harvested and proliferated to populate the implant structure prior to implantation, or through the porous membrane after implantation. Preferably, mesenchymal stem cells will be harvested and may be provided from a donor or from the patient's adipose or bone marrow. Proliferating and differentiation of these cells is well understood along with the potency of the cells often associated with patient age. In the case of an elderly patient, it may be preferred to have a donor source or a donor bank. It also possible to proliferate the patient's differentiated (adult) cells for the epithelium and the nonstriated muscle fibers in addition to the ECM extruded by fibroblasts and forming the wall of the implant or neourethral structure. The catheter system may be used to facilitate growth of the neourethra in a bioreactor vessel ex vivo or in the preferred in vivo process described.

The collagen-based scaffold may be attached to, and/or grown into and/or around tissue of the human body. The collagen-based scaffold may be implanted with a catheter similar to the process described above. For instance, a first end of the collagen-based scaffold can be secured to a body conduit such as the urethra and a second end of the collagen-based scaffold can be secured to tissue such as a bladder. However, with the collagen-based scaffold rebuilt/regrown ex vivo with the human cells prior to an implantation procure, the implantation procedure will be expedited.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Referring also to FIG. 10, a medical work station is shown generally as work station 1000 and generally may include a plurality of robot arms 1002, 1003; a control device 1004; and an operating console 1005 coupled with the control device 1004. The operating console 1005 may include a display device 1006, which may be set up in particular to display three-dimensional images; and manual input devices 1007, 1008, by means of which a person (not shown), for example a clinician, may be able to telemanipulate the robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100 (e.g., a pair of jaw members), in accordance with any one of several embodiments disclosed herein, as will be described in greater detail below.

The robot arms 1002, 1003 may be driven by electric drives (not shown) that are connected to the control device 1004. The control device 1004 (e.g., a computer) may be set up to activate the drives, in particular by means of a computer program, in such a way that the robot arms 1002, 1003, their attaching devices 1009, 1011 and thus the surgical tool (including the end effector 1100) execute a desired movement according to a movement defined by means of the manual input devices 1007, 1008. The control device 1004 may also be set up in such a way that it regulates the movement of the robot arms 1002, 1003 and/or of the drives.

The medical work station 1000 may be configured for use on a patient "P" lying on a patient table 1012 to be treated in a minimally invasive manner by means of the end effector 1100. The medical work station 1000 may also include more than two robot arms 1002, 1003, the additional robot arms likewise connected to the control device 1004 and telemanipulatable by means of the operating console 1005. A medical instrument or surgical tool (including an end effector 1100) may also be attached to the additional robot arm. The medical work station 1000 may include a database 1014 coupled with the control device 1004. In some embodiments, pre-operative data from patient/living being "P" and/or anatomical atlases may be stored in the database 1014.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. A method for coupling a body conduit to tissue, the method comprising:
    seeding a collagen-based scaffold with cells;
    mounting the collagen-based scaffold on a catheter;
    positioning the collagen-based scaffold within a body to provide a bridge between a conduit and a tissue opening each defined in the body; and
    maintaining the catheter and the collagen-based scaffold in the body while the collagen-based scaffold forms a permanent connection with the conduit and the tissue opening,
    wherein the collagen-based scaffold maintains the conduit and the tissue opening spaced from one another as the permanent connection is formed.

2. The method according to claim 1, wherein the cells are human stem cells, the method further comprising changing a morphology of the human stem cells to render the collagen-based scaffold suitable for implantation within the body.

3. The method according to claim 2, further comprising forming the collagen-based scaffold from a decellularized xenograft.

4. The method according to claim 3, further comprising harvesting the xenograft from porcine tissue.

5. The method according to claim 4, wherein the porcine tissue is a porcine urethra.

6. The method according to claim 2, wherein changing the morphology of the human stem cells includes effecting a differentiation of the human stem cells.

7. The method according to claim 6, wherein the differentiation of the human stem cells occurs ex vivo.

8. The method according to claim 1, further comprising embedding the collagen-based scaffold with a bioactive agent having tissue growth properties, wherein the bioactive agent facilitates securing the collagen-based scaffold to the conduit and the tissue opening.

9. A method for coupling a body conduit to tissue, the method comprising:
    positioning a collagen-based scaffold about a catheter;
    inserting the catheter through a body conduit of a human body and into a tissue opening defined in the human body, thereby positioning the collagen-based scaffold in a resected area defined between the tissue opening and the body conduit, the tissue opening spaced from the body conduit to define the resected area;
    maintaining the catheter and the collagen-based scaffold in the human body while the collagen-based scaffold forms a connection with the body conduit and the tissue opening, wherein the collagen-based scaffold maintains the body conduit and the tissue opening spaced from one another for a time sufficient to enable new tissue growth to form between the collagen-based scaffold and the body conduit and the collagen-based scaffold and the tissue opening; and seeding the collagen-based scaffold with human stem cells.

10. The method according to claim 9, further comprising changing a morphology of the human stem cells to render the collagen-based scaffold suitable for implantation within the human body.

11. The method according to claim 10, further comprising forming the collagen-based scaffold from a decellularized xenograft.

12. The method according to claim 11, further comprising harvesting the xenograft from porcine tissue.

13. The method according to claim 12, wherein the porcine tissue is a porcine urethra.

14. The method according to claim 10, wherein changing the morphology of the human stem cells includes effecting a differentiation of the human stem cells.

15. The method according to claim 14, wherein the differentiation of the human stem cells occurs ex vivo.

16. The method according to claim 9, further comprising embedding the collagen-based scaffold with a bioactive agent having tissue growth properties, wherein the bioactive agent facilitates securing the collagen-based scaffold to the body conduit and the tissue opening.

17. The method according to claim 9, further comprising inflating a balloon of the catheter to anchor the catheter within the tissue opening such that the collagen-based scaffold bridges the body conduit and the tissue opening across the resected area.

* * * * *